US00PP37420P2

(12) United States Plant Patent
Zlesak et al.

(10) Patent No.: US PP37,420 P2
(45) Date of Patent: May 12, 2026

(54) ***HYDRANGEA* PLANT NAMED 'BAICZ10'**

(50) Latin Name: *Hydrangea arborecens*
Varietal Denomination: BAICZ10

(71) Applicant: Bailey Nurseries, Newport, MN (US)

(72) Inventors: David Charles Zlesak, River Falls, WI (US); Gail Katherine Soens, Woodbury, MN (US)

(73) Assignee: BAILEY NURSERIES INC, Newport, MN (US)

( * ) Notice: Subject to any disclaimer, the term of this patent is extended or adjusted under 35 U.S.C. 154(b) by 0 days.

(21) Appl. No.: 19/300,755

(22) Filed: Aug. 15, 2025

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./250
See application file for complete search history.

*Primary Examiner* — Susan Mccormick Ewoldt
*Assistant Examiner* — Zachariah Allan Kay
(74) *Attorney, Agent, or Firm* — Penny J. Aguirre

(57) ABSTRACT

A new cultivar of *Hydrangea arborescens* plant named 'BAICZ10' that is characterized by its strong branches that resist lodging, its symmetrical and dense plant habit, its mophead medium-sized inflorescences with medium-sized sterile flowers, its inflorescences borne around the overall perimeter of the plant, its bright and vibrant rosy-pink sterile sepal color upon opening with sepal color transitioning sequentially to pink, a greyed-red color with a green background, green, and finally tan by the end of the growing season, and its dark green foliage color over a broad range of soil conditions.

3 Drawing Sheets

Botanical classification: *Hydrangea arborescens*.
Varietal denomination: 'BAICZ10'.

BACKGROUND OF THE INVENTION

The present invention relates to a new and distinct cultivar of *Hydrangea arborescens* and will be referred to hereafter by its cultivar name, 'BAICZ10'. 'BAICZ10' represents a new smooth *Hydrangea*, a perennial shrub grown for landscape use.

'BAICZ10' was derived from an ongoing breeding program by the inventors in Cottage Grove, Minnesota. The goal of the breeding program is to create new cultivars of *Hydrangea* with strong stems, abundant blooms, compact and dense plant habits, good winter hardiness, uniform plant habit, resistance to foliar diseases, and ease of propagation and production. 'BAICZ10' originated from the cross pollination of two proprietary, non-patented, pink-flowered selections in 2019. 'BAICZ10' germinated in the greenhouse early February 2020 and was identified by April 2020 as having a desirable plant habit relative to its siblings, selected, and transplanted to a larger container. The original plant of 'BAICZ10' continued to be retained through additional cycles of selection due to its desirable plant habit and was field planted in July 2020.

Asexual propagation of the new cultivar was first accomplished by softwood stem cuttings by one of the inventors in summer of 2022 in Cottage Grove, Minnesota. Asexual propagation by softwood and semi-hardwood stem cuttings has determined that the characteristics of the new cultivar are stable and are reproduced true to type in successive clonal generations.

SUMMARY OF THE INVENTION

The following traits have been repeatedly observed and represent the characteristics of the new cultivar. These attributes in combination distinguish 'BAICZ10' as a unique cultivar of *Hydrangea arborescens*.

1. 'BAICZ10' exhibits strong branches that resist lodging.
2. 'BAICZ10' exhibits a symmetrical and dense plant habit.
3. 'BAICZ10' exhibits mophead medium-sized inflorescences with medium-sized sterile flowers.
4. 'BAICZ10' exhibits inflorescences borne around the overall perimeter of the plant.
5. 'BAICZ10' exhibits a bright and vibrant rosy-pink sepal color upon opening with sepal color transitioning sequentially to pink, a greyed-red color with a green background, green, and finally tan by the end of the growing season.
6. 'BAICZ10' exhibits dark green foliage color over a broad range of soil conditions.

The maternal parent of 'BAICZ10' differs from 'BAICZ10' in that 'BAICZ10' has more intensely pink-colored blooms as they open, sepals that age with a reddish-colored overlay on the sepals versus green, and that 'BAICZ10' starts to flower a little bit later than its maternal parent in the landscape in Cottage Grove, Minnesota. The specific paternal parent of 'BAICZ10' is not known. Two similar and proprietary, non-patented pink-flowered selections were used as male parents on different inflorescences of the maternal parent plant. Seed was bulked from the two crosses that shared the same maternal parent to create the seedling population from which 'BAICZ10' was selected. 'BAICZ10' has more intense pink colored flowers upon opening than either of the two genotypes that were used as males to generate the population. 'BAICZ10' is most similar to *Hydrangea arborescens* cultivars 'NCHA3' (U.S. Plant Pat. No. 28,317) and 'NCHA4' (U.S. Plant Pat. No. 28,280). 'NCHA3' and 'NCHA4' are similar to 'BAICZ10' in having flowers that open pink in color. 'BAICZ10' has a brighter, more vibrant opening pink flower color, sterile florets that age with more red tones, and grows into a larger plant in USDA cold hardiness zone 4 than both 'NCHA3' and 'NCHA4'.

BRIEF DESCRIPTION OF THE DRAWINGS

The accompanying color photographs illustrate the overall appearance and distinct characteristics of the new *Hydrangea*. The photographs were taken of a plant five years in age as grown outdoors in a trial plot in Cottage Grove, Minnesota.

The photograph in FIG. 1 provides a view of inflorescences of 'BAICZ10' with brightly colored and expanding sepals of the sterile florets.

Figure 1:
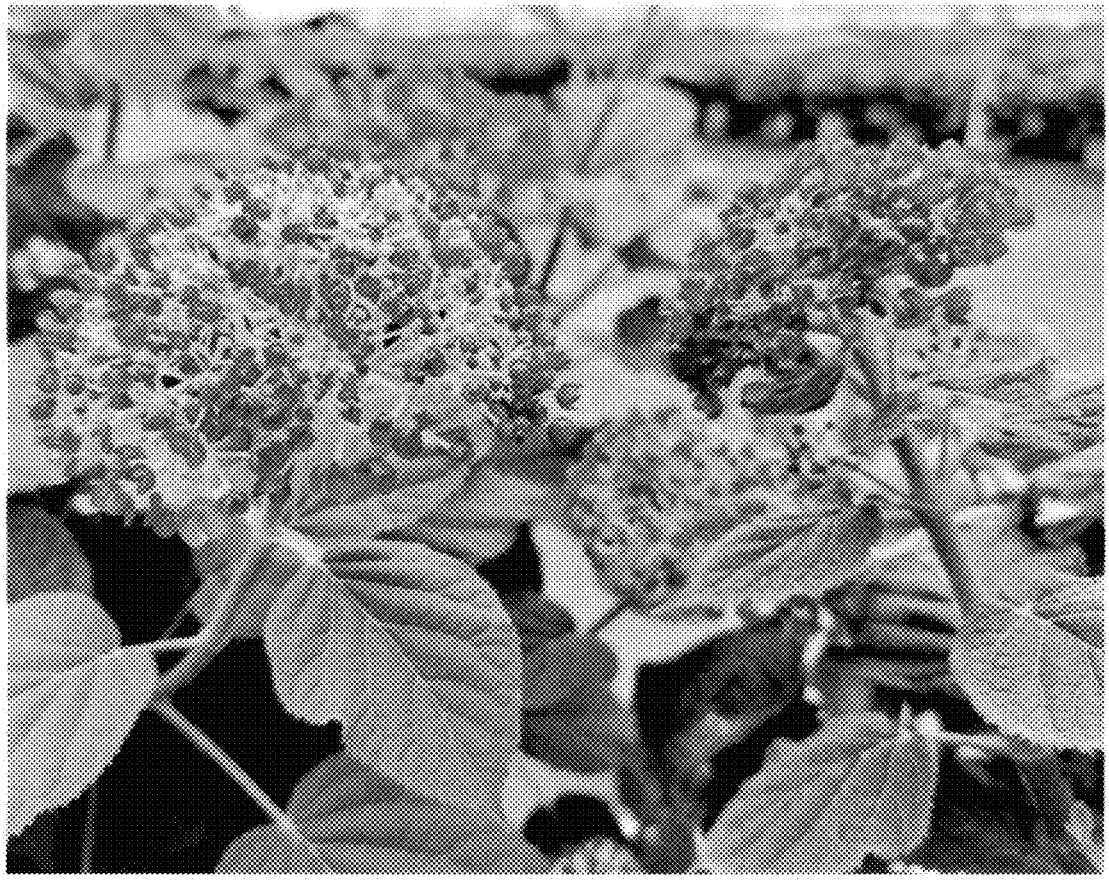
Figure 2:
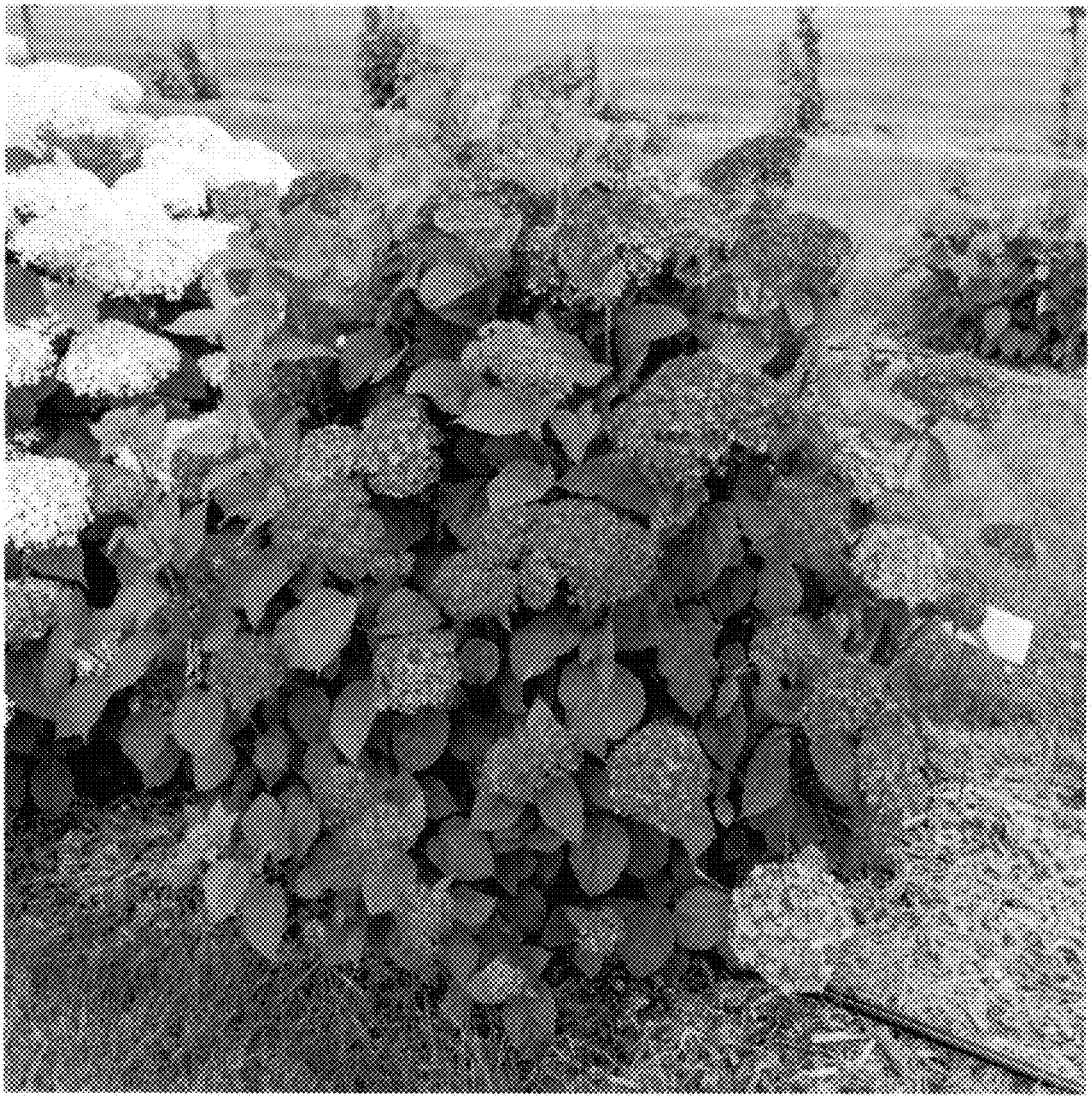

The photograph in FIG. 2 provides a view of a whole plant of 'BAICZ10' coming into full flower.

Figure 3:
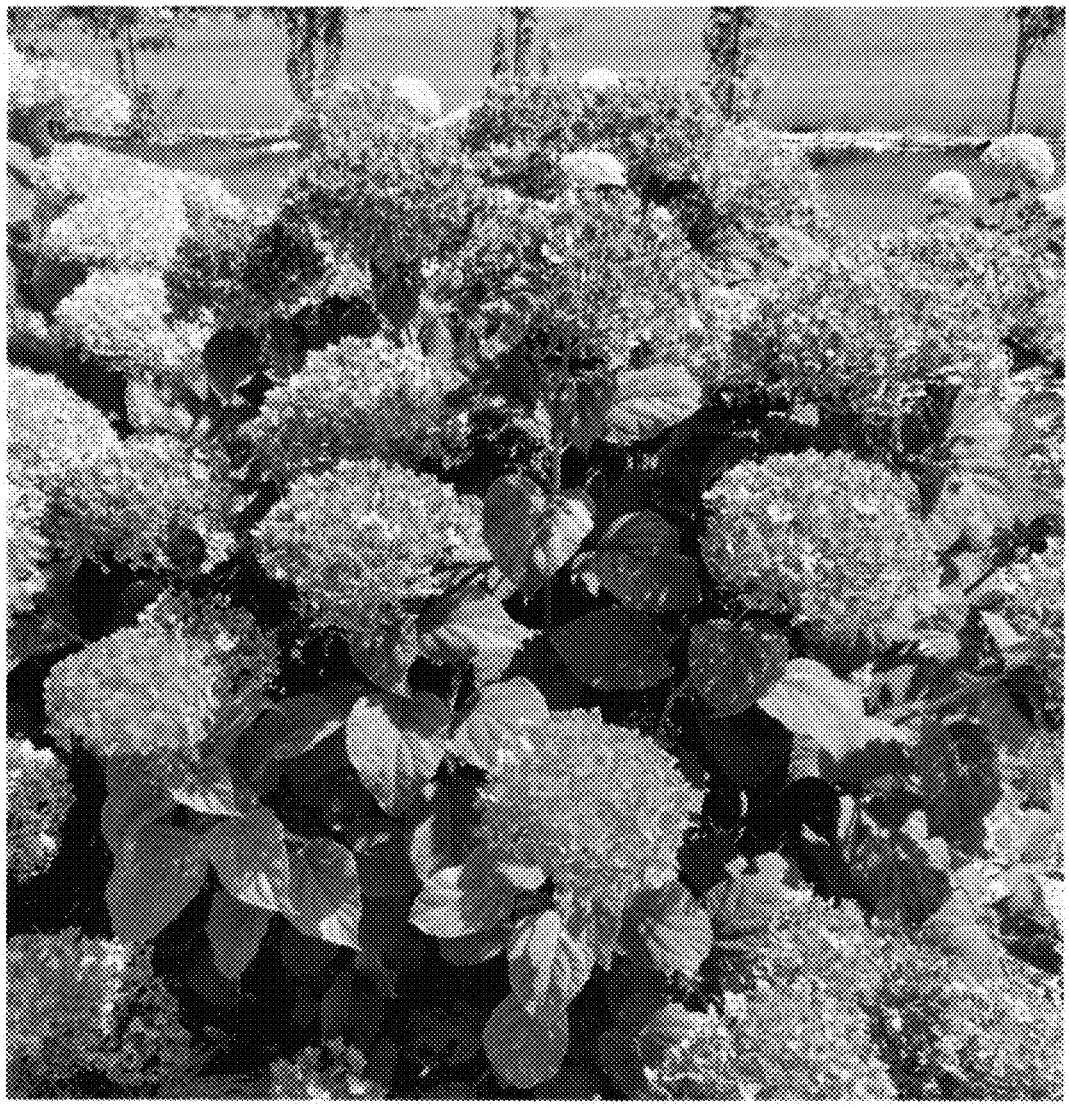

The photograph in FIG. 3 provides a view of aging inflorescences displaying a reddish overlay of color on the sepals of 'BAICZ10'.

The colors in the photographs are as close as possible with the photographic and printing technology utilized and the color values cited in the detailed botanical description accurately describe the colors of the new *Hydrangea*.

BOTANICAL DESCRIPTION OF THE PLANT

The following is a detailed description of plants two years in age in 2-gallon containers in June 2025 in Cottage Grove, Minnesota, unless otherwise noted. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—From mid-June through mid-July for main flush with some continued flowering possible into fall in Minnesota.

*Plant type*.—Perennial shrub with mophead-like flowerheads.

*Plant habit*.—Sturdy and straight stems, rounded silhouette, and dense growth.

*Height and spread*.—The ortet was 92 cm in height and 122 cm in width during its sixth growing season in the field in June 2025.

*Cold hardiness*.—At least to U.S.D.A. Zone 4.

*Diseases and pests*.—Resistance to bacterial leaf spot caused by *Xanthomonas campestris*.

*Root description*.—Fibrous.

*Time required for root development*.—2 weeks for root initiation, 6 weeks to produce a fully rooted plug.

Stem description:

*Stem shape*.—Rounded.

*Stem strength*.—Strong, resists lodging.

*Stem aspect*.—Upright to slightly outward.

*Stem color*.—Young; 139D, heavily flushed with 183A, mature and older bark; N199C with vertical striations of N199C.

*Stem size*.—An average of 50 cm (excluding the inflorescence) in length and 0.5 to 1.0 cm in diameter.

*Stem surface*.—Young; dull and densely tomentose with soft matted hairs, hairs slightly translucent and 196B, 0.2-0.3 mm in length and 0.05 mm in width, mature; glabrous and slightly glossy.

*Branching*.—Freely branched with 94 lateral branches each terminating in an inflorescence on the six year-old ortet growing in the field in June 2025.

*Internode length*.—A typical range of 4-6 cm.

Foliage description:

*Leaf shape*.—Ovate.

*Leaf arrangement*.—Opposite.

*Leaf division*.—Simple.

*Leaf number*.—Typically 12-18 per lateral branch.

*Leaf base*.—Cordate.

*Leaf apex*.—Apiculate.

*Leaf margins*.—Dentate to serrate.

*Leaf venation*.—Pinnate, upper surface 138D in color, lower surface 139D, densely tomentose with soft matted hairs that are 196C and are 0.2-0.3 mm in length and 0.05 mm in width.

*Leaf lamina size*.—Typically 11-13 cm in length, 8.5-10.5 cm in width.

*Leaf attachment*.—Petiolate.

*Leaf surface*.—Upper surface; dull and slightly rugose, lower surface; moderately rugose, upper surface tomentose with short stiff hairs, 0.3 mm in length, NN155D in color, lower surface relatively glabrous with more sparsely spaced hairs that are similar in color and size to the hairs on the upper surface.

*Leaf color*.—Young; upper surface 137C, Mature: upper surface 137A, Young and Mature: lower surface N138C.

*Petioles*.—Typically 4.0-7.5 cm in length and 3 mm in diameter, 144C, heavily flushed in bright light with 183A, both surfaces dull and densely tomentose with soft matted hairs, slightly translucent and 196B, 0.3 mm long and 0.05 mm in width.

Inflorescence description:

*Inflorescence type*.—Round, flattened, mophead, compound corymb of rotate-shaped sterile flowers over fertile flowers.

*Lastingness of inflorescence*.—Sterile and fertile flowers; an average of 4 weeks for all inflorescences to open during the primary flowering cycle in late spring to early summer, sterile flowers persistent, fertile flowers self-cleaning.

*Inflorescence number*.—One per lateral stem.

*Inflorescence size*.—Typically 9-10 cm in depth and 14-21 cm in diameter.

*Flower number*.—An average of approximately 450 sterile flowers and 300 fertile flowers per typical inflorescence.

*Flower fragrance*.—Light, sweet scent.

*Flower aspect*.—Sterile and fertile flowers; borne around the perimeter of the rounded, slightly flattened inflorescence (i.e., flowers are oriented upright near the top, outwards near the center, and slightly downward around the bottom of the inflorescence).

*Flower size*.—Fully expanded sterile flowers; typically 1.5 to 2.5 cm in diameter and 4 mm in depth, fertile flowers; typically 0.5 to 1.0 cm in diameter and 5 mm in depth.

*Flower shape*.—Sterile flowers; rotate, fertile flowers; rotate.

*Flower buds before opening*.—Upon flower buds first being visible the sterile and fertile florets are indistinguishable from each other, flower buds are 1 mm in diameter and height and 145C, as flower buds advance in age before opening, sterile and fertile florets become distinguishable, sterile flowers; 3 mm in diameter, 3 mm in depth, rounded to slightly flattened, color; 145C transitioning to 58A, fertile flowers; 2 mm in diameter and 2 mm in depth, rounded in shape, color; 142D.

*Peduncles*.—The overall branched peduncle in an inflorescence is on average 8 cm in total length and 1-3 mm in diameter, 143C, flushed with 183A, surfaces dull and densely tomentose with soft matted hairs, slightly translucent and 196B, too small to measure size.

*Pedicels*.—Sterile flowers; average of 1.5 to 2.5 cm in length, 1 mm in diameter, Fertile flowers; 3-5 mm in length and 0.8 mm in diameter, pedicels of both sterile and fertile of flowers are 143C in color with an overlay of 183A, dull surface that is densely tomentose with soft matted hairs, slightly translucent and 196B, too small to measure size.

*Petals*.—Sterile flowers; 3 to 4 petals that frequently adhere to each other preventing opening and leading to them persisting, 0.5 mm in length, 0.3 mm in width, elliptic in shape, color; young 142C, mature 63C, fertile flowers; 5, 2 mm in length, 1 mm in width, ovate in shape, color; 155C from opening to abscission.

*Sepals*.—Sterile flowers; an average of 4 to 5 per flower, rotate in arrangement, ovate in shape, very slightly concave, rounded to very short apiculate apex, rounded to widely acute base, entire margin, an average of 12 mm in length and 11 mm in width when fully expanded, both surfaces; glabrous, smooth, velvety, color; upper and lower surface similar throughout their life starting at 58A when they begin to expand and then transitioning to 61B during continued expansion and then to 63C when sepals are fully expanded, as sepals age, they transition to 145B with an overlay of 60C with a more intense overlay typically on the lower sepal surface, by autumn the sepals dry and become 161D in color, fertile flowers; rotate in arrangement, angled upward from point of attachment on the ovary, flat, deltoid in shape, truncate base, acute apex, entire margin, an average of 1 mm in length and 1 mm in width, color: upper and lower surface when opening and through to maturity 142C, sepals are persistent and at the end of the season when dry are 161D.

Reproductive organs:

*Gynoecium*.—Sterile flowers; none observed, fertile flowers; perigynous, compound pistil with two or rarely three carpels per flower, typically 2.5-3.0 mm in length, stigmas; separate and club shaped, 1.0 mm in length and 0.5 mm in diameter, angled outward from each other, 155C in color, style; 0.5 mm in length and 0.5 mm in diameter, 155C in color, ovary; globular and 1.5 mm in length and width, color 137B.

*Androecium*.—Sterile flowers; typically none observed, but periodically 3-5 stamens, filaments 2-3 mm in length and 0.3 mm in diameter, color 155C, anthers 0.5 mm in length and width, color; 160C, pollen; sparce, color NN155B, fertile flowers; 8-10 stamens, filaments; 3-5 mm in length and 0.3 mm in diameter, color; 155C, anthers; 0.5 mm in length and width, color 160C, pollen; moderate, color NN155B.

*Fruit and seed*.—Capsules are generally globular in shape with persistent sepals and stigmas, 2-3 mm in length and width, color at maturity, 165A, seeds, abundant and small, 0.8-1.0 mm in length and 0.15 mm in width, color, 164A.

It is claimed:

1. A new and distinct cultivar of *Hydrangea* plant named 'BAICZ10' substantially as herein illustrated and described.

* * * * *